(12) United States Patent
Ma et al.

(10) Patent No.: US 11,478,636 B2
(45) Date of Patent: *Oct. 25, 2022

(54) TUBE-CUT HELICAL FIXATION ANCHOR FOR ELECTROTHERAPY DEVICE

(71) Applicant: Pacesetter, Inc., Sylmar, CA (US)

(72) Inventors: Ivan Ma, San Mateo, CA (US); Bruce Weir, Plymouth, MN (US); Matthew G. Fishler, Scotts Valley, CA (US); Ott Khouengboua, Chaska, MN (US)

(73) Assignee: PACESETTER, INC., Sylmar, CA (US)

( * ) Notice: Subject to any disclaimer, the term of this patent is extended or adjusted under 35 U.S.C. 154(b) by 579 days.

This patent is subject to a terminal disclaimer.

(21) Appl. No.: 16/506,879

(22) Filed: Jul. 9, 2019

(65) Prior Publication Data
US 2019/0329031 A1 Oct. 31, 2019

Related U.S. Application Data

(63) Continuation of application No. 14/852,209, filed on Sep. 11, 2015, now Pat. No. 10,391,306.

(51) Int. Cl.
*A61N 1/05* (2006.01)
*A61N 1/375* (2006.01)

(52) U.S. Cl.
CPC ......... *A61N 1/0573* (2013.01); *A61N 1/3756* (2013.01)

(58) Field of Classification Search
CPC .......................... A61N 1/0573; A61N 1/3756
See application file for complete search history.

(56) References Cited

U.S. PATENT DOCUMENTS

| 8,755,909 | B2 | 6/2014 | Sommer et al. |
| 2007/0088394 | A1 | 4/2007 | Jacobson |
| 2007/0088396 | A1 | 4/2007 | Jacobson |
| 2007/0088397 | A1 | 4/2007 | Jacobson |
| 2007/0088398 | A1 | 4/2007 | Jacobson |
| 2007/0088400 | A1 | 4/2007 | Jacobson |
| 2007/0088405 | A1 | 4/2007 | Jacobson |
| 2007/0088418 | A1 | 4/2007 | Jacobson |

(Continued)

FOREIGN PATENT DOCUMENTS

WO 2007/047681 A2 4/2007

OTHER PUBLICATIONS

NonFinal Office Action dated Oct. 11, 2016—parent case U.S. Appl. No. 14/852,209.

(Continued)

*Primary Examiner* — Joseph M Dietrich
(74) *Attorney, Agent, or Firm* — Womble Bond Dickinson (US) LLP

(57) ABSTRACT

An implantable medical device is disclosed herein and can be in the form of an implantable medical lead or a leadless pulse generator. The implantable medical device includes a body, at least one electrode and a tube-cut helical fixation anchor. The body includes a distal end and a proximal end opposite the distal end. The at least one electrode is supported on the body. The tube-cut helical fixation anchor distally extends from the distal end. The tube-cut helical fixation anchor may be fixed or extendable/retractable relative to the distal end. The tube-cut helical fixation anchor may be a result of a manufacturing process comprising cutting the tube-cut helical fixation anchor from a thin-walled tubular body.

20 Claims, 13 Drawing Sheets

(56) References Cited

U.S. PATENT DOCUMENTS

2010/0222855 A1 9/2010 Hill et al.
2010/0234931 A1 9/2010 Jari et al.
2012/0116489 A1 5/2012 Khairkhahan et al.
2015/0351910 A1 12/2015 Gillmore et al.

OTHER PUBLICATIONS

NonFinal Office Action dated Jul. 3, 2017—parent case U.S. Appl. No. 14/852,209.
NonFinal Office Action dated May 23, 2018—parent case U.S. Appl. No. 14/852,209.
Final Office Action dated Jan. 17, 2017—parent case U.S. Appl. No. 14/852,209.
Final Office Action dated Jan. 12, 2018—parent case U.S. Appl. No. 14/852,209.
NonFinal Office Action dated Jan. 11, 2019—parent case U.S. Appl. No. 14/852,209.
Notice of Allowance dated Apr. 12, 2019—parent case U.S. Appl. No. 14/852,209.

US 11,478,636 B2

TUBE-CUT HELICAL FIXATION ANCHOR FOR ELECTROTHERAPY DEVICE

CROSS REFERENCE TO RELATED APPLICATIONS

This application is a continuation and claims priority to U.S. patent application Ser. No. 14/852,209 filed Sep. 11, 2015, which is Incorporated herein by reference.

FIELD OF THE INVENTION

Aspects of the present invention relate to medical apparatus and methods. More specifically, the present disclosure relates to helical fixation anchors for use with implantable medical leads and leadless pulse generators. The present disclosure also relates to methods of manufacturing and using such helical fixation anchors.

BACKGROUND OF THE INVENTION

Traditionally, implantable medical leads and leadless pulse generators have been actively anchored in cardiac tissue (e.g., epicardium, myocardium, endocardium, trabeculae, pectinate muscle, etc.) via helical fixation anchors. As can be understood from FIG. 1, which is a side elevation of such a prior art helical fixation anchor 1, these prior art helical fixation anchors 1 are manufactured from a segment of extruded round diameter wire 2 that is wound into a helical configuration. Such wound-wire helical anchors 1 have many inherent limitations. Consequently, there is a need in the art for an improved helical fixation anchor configuration and related methods of manufacture and use.

BRIEF SUMMARY OF THE INVENTION

An implantable medical device is disclosed herein. The implantable medical device includes a body, at least one electrode and a tube-cut helical fixation anchor. The body includes a distal end and a proximal end opposite the distal end. The at least one electrode is supported on the body. The tube-out helical fixation anchor distally extends from the distal end. The tube-cut helical fixation anchor may be fixed or extendable/retractable relative to the distal end. The tube-cut helical fixation anchor may be a result of a manufacturing process comprising cutting the tube-cut helical fixation anchor from a thin-walled tubular body. Depending on the embodiment, the implantable medical device can include an implantable medical lead or a leadless pulse generator.

In one embodiment, the tube-cut helical fixation anchor includes a retained cylindrical wall portion of the thin-wall tubular body. The retained cylindrical wall portion interrupts a helical cut defined in the thin-wall tubular body to define helical turns of the tube-cut helical fixation anchor. The cylindrical wall portion extends uninterrupted between adjacent helical turns of the helical turns of the tube-cut helical fixation anchor.

Depending on the embodiment, the tube-cut helical fixation anchor includes a helical turn comprising a rectangular cross-section or a cross-section of a parallelogram with a first pair of opposite corner angles and a second pair of opposite corner angles, wherein the first pair are different than the second pair.

In one embodiment, the tube-cut helical fixation anchor includes a helical turn comprising distal and proximal parallel flat helically extending surfaces that are oblique relative to a longitudinal center axis of the tube-cut helical fixation anchor.

In one embodiment, the tube-cut helical fixation anchor includes a helical turn comprising distal and proximal parallel flat helically extending surfaces, the helical turn further including a barb extending from at least one of the flat helically extending surfaces.

In one embodiment, the tube-cut helical fixation anchor includes first and second helical turns, wherein the first helical turn has a cross-sectional height that is less than a cross-section height of the second helical turn.

In one embodiment, the tube-cut helical fixation anchor includes first and second adjacent helical turns, wherein a distal-proximal bend in at least one of the first or second adjacent helical turns results in a reduced gap spacing between the first and second adjacent helical turns as compared to other locations on the tube-cut helical fixation anchor. In one embodiment, the tube-cut helical fixation anchor includes helical turns having a varied helical pitch along the length of the tube-cut helical fixation anchor.

Another implantable medical device is also disclosed herein. The implantable medical device may be in the form of an implantable medical lead or a leadless pulse generator. In one embodiment the implantable medical device includes a body, and electrode and a helical fixation anchor. The body includes a distal end and a proximal end opposite the distal end. The electrode is supported on the body. The helical fixation anchor distally extends from the distal end and includes a helical turn including a quadrilateral cross-section. The quadrilateral cross-section includes a cross-sectional height and a cross-sectional width that is greater than the cross-sectional height.

Depending on the embodiment, the quadrilateral cross-section is a rectangle or a parallelogram with a first pair of equal opposite corner angles and a second pair of equal opposite corner angles, wherein the first pair are different than the second pair.

In one embodiment, the helical turn includes flat helically extending distal and proximal surfaces, and a barb extends from at least one of the distal or proximal surfaces.

In one embodiment, the helical turn includes flat helically extending distal and proximal surfaces, and a cross-sectional height between the distal and proximal surfaces varies along a helical length of the helical turn.

In one embodiment, the helical turn includes a barbed tip defined by a variation in the cross-sectional height of the quadrilateral cross-section extending along a helical length of the helical turn.

In one embodiment, the helical turn changes pitch along a helical length of the helical turn.

In one embodiment, the helical turn bends distal-proximal to form a bend in the helical turn that deviates from a pitch of the helical turn adjacent to the bend.

In one embodiment, the helical fixation anchor comprises a cylindrical wall portion that interrupts a helical slot separating adjacent turns of the helical turn. The cylindrical wall portion extends uninterrupted between adjacent turns of the helical fixation anchor.

Also disclosed herein is a method of manufacturing a helical fixation anchor for an implantable medical device. In one embodiment, the method includes cutting a helical slot through a wall of a thin-wall tubular body, the helical slot extending helically about a circumference of the thin-wall tubular body and defining helical turns of the resulting helical fixation anchor. In some embodiments, the cutting includes mechanical, chemical or energy cutting methods.

The mechanical cutting can include water jet cutting or other mechanical cutting methods. The energy cutting can include laser cutting, plasma cutting or other energy cutting methods. Other manufacturing methods may include wire EDM and micro injection molding of metal or polymer.

While multiple embodiments are disclosed, still other embodiments of the present disclosure will become apparent to those skilled in the art from the following detailed description, which shows and describes illustrative embodiments of the disclosure. As will be realized, the invention is capable of modifications in various aspects, all without departing from the spirit and scope of the present disclosure. Accordingly, the drawings and detailed description are to be regarded as illustrative in nature and not restrictive.

BRIEF DESCRIPTION OF THE DRAWINGS

The description will be more fully understood with reference to the following figures, which are presented as various embodiments of the disclosure and should not be construed as a complete recitation of the scope of the disclosure, wherein.

DETAILED DESCRIPTION

The present disclosure provides improved active helical fixation anchors 66 for use with implantable medical leads or leadless pulse generators. Such improved active helical fixation anchors 66 are helically cut from a tube. These tube-cut helical fixation anchors 66 can extend from a distal end of an implantable medical lead or a distal end of a leadless pulse generator. In either case, the tube-cut helical fixation anchors 66 disclosed herein provide enhanced tissue anchoring capability as compared to those wound-wire helical fixation anchors 1 known in the art and reflected in FIG. 1. The anchors 66 disclosed herein also providing manufacturing advantages such as, for example, having features to aid the assembly of the anchor to an implantable medical lead or leadless pulse generator. Other advantages of the anchors will become apparent throughout this Detailed Description.

Figure 1:
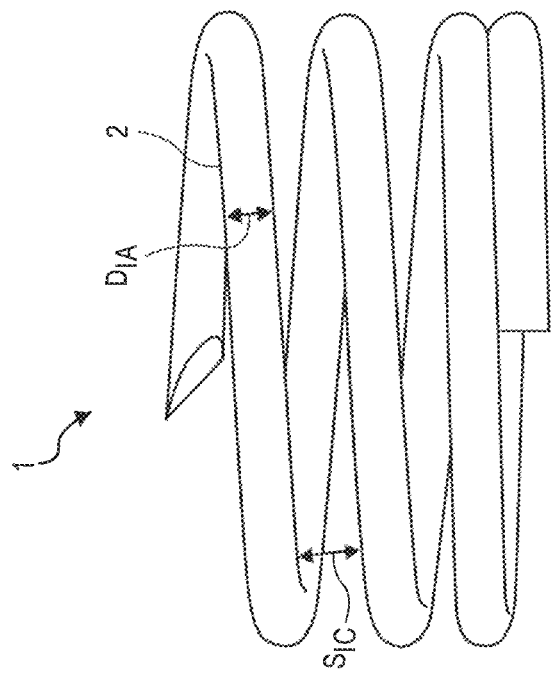
FIG. 1 is a side elevation of a prior art helical fixation anchor formed from a round diameter wire wound into a helical configuration.

Unlike the prior art wound-wire helical fixation anchor 1 of FIG. 1, which is formed from a round cross-section extruded wire 2 that is has been helically wound, the tube-cut helical fixation anchor 66 disclosed herein has a cross-section that is a quadrilateral and is formed by cutting a helical geometry out of a tube. By cutting a helical fixation anchor 66 out of material that is initially a tube, unique features can be achieved as compared to using round cross-section wire to create a prior art wound-wire fixation anchor 1. These unique features of the tube-cut helical fixation anchor 66 can solve challenges in fixating a device into cardiac tissue, including those challenges that are especially difficult in the context of fixating a leadless pulse generator in the right atrium, including, for example, thin atrial tissue, helical fixation anchors that can protrude out of the atrium and irritate or attach to the pericardium, and device dislodgement due to lack of tissue engagement and/or excessive movement.

Before beginning a discussion regarding the details of the tube-cut helical active fixation anchors 66 disclosed herein, a general discussion will first be given regarding electrotherapy systems employing a pulse generator and lead(s), followed by a general discussion of electrotherapy systems employing leadless pulse generators, both of which can employ any of the tube-cut helical active fixation anchors disclosed herein.

a. Electrotherapy System Employing Pulse Generator and Lead(s)

Figure 2A:
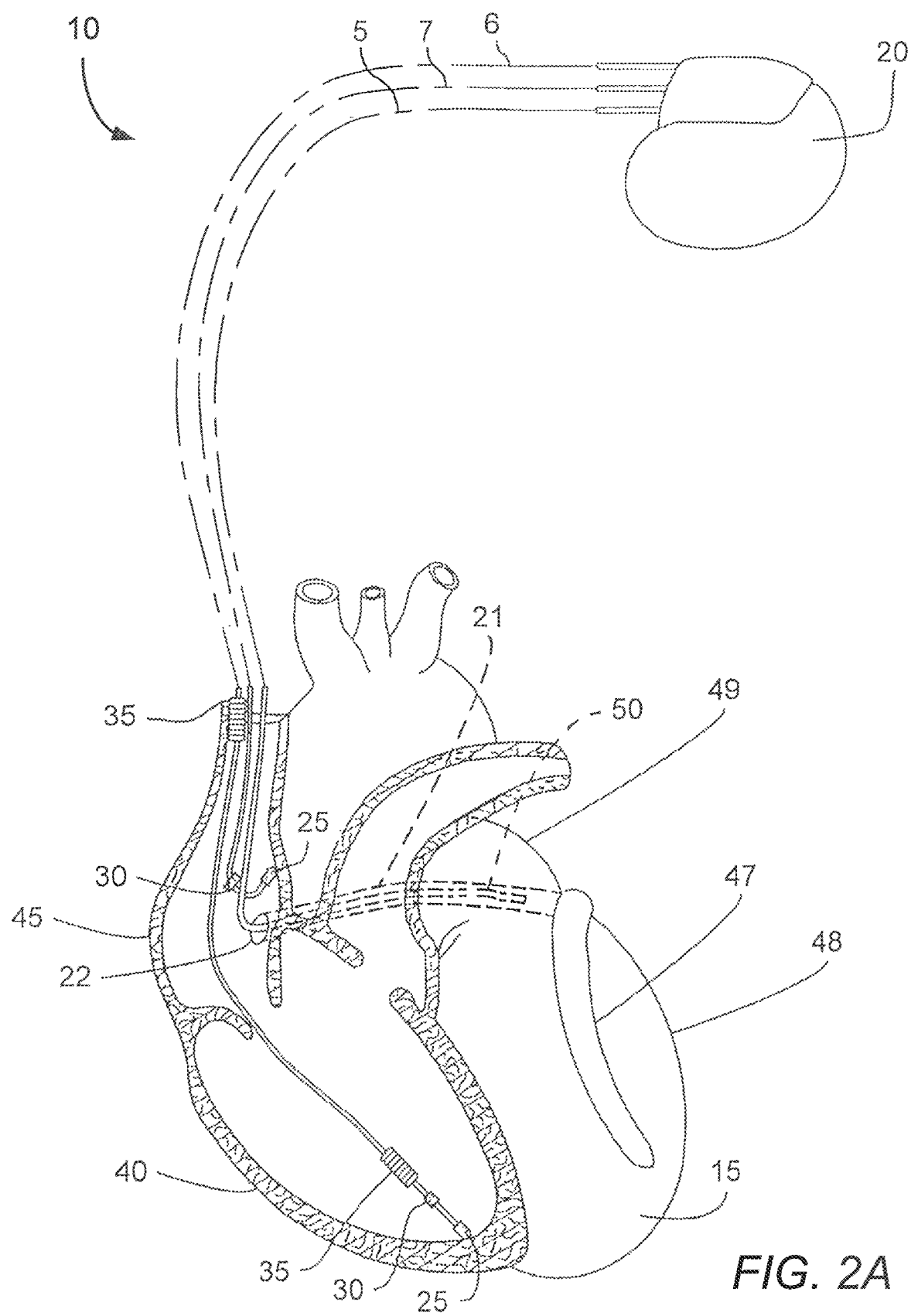
FIG. 2A is a diagrammatic depiction of a traditional electrotherapy system electrically coupled to a patient heart as viewed from an anterior side of the patient heart.

FIG. 2A is a diagrammatic depiction of a traditional electrotherapy system 10 electrically coupled to a patient heart 15 as viewed from an anterior side of the patient heart. As shown in FIG. 2A, the system 10 includes an implantable pulse generator 20 (e.g., pacemaker, implantable cardioverter defibrillator (ICD), or etc.) and one or more (e.g., three) implantable medical leads 5, 6, 7 electrically coupling the patient heart 15 to the pulse generator 20. Depending on the type of electrotherapy to be administered to the patient, the system 10 may employ a variety of lead types, combinations and implantation target sites. For example, as can be understood from FIG. 2A, the system 10 may have a left ventricular (LV) lead 5, a right ventricular (RV) lead 6 and/or a right atrial (RA) lead 7. The LV lead 5 may extend into the coronary sinus (CS) 21 via the coronary sinus ostium (OS) 22. In some implantation arrangements, the LV lead 5 may even further extend into the great cardiac vein or coronary vein 47 or a branch thereof. The RV lead 6 may extend through the right atrium 45 and into the right ventricle 40. The RA lead 7 may extend into the right atrium 45. The RV and RA leads 6, 7 may employ pacing electrodes 25, sensing electrodes 30 and shock cons 35 as known in the art to respectively provide electrical stimulation to the right ventricle 40 and right atrium 45 of the heart 15. The distal region 50 of the LV lead 5 may be similarly equipped with electrodes and coils so as to provide similar electrical stimulation to the left ventricle 48 and/or the left atrium 49.

Figure 2B:
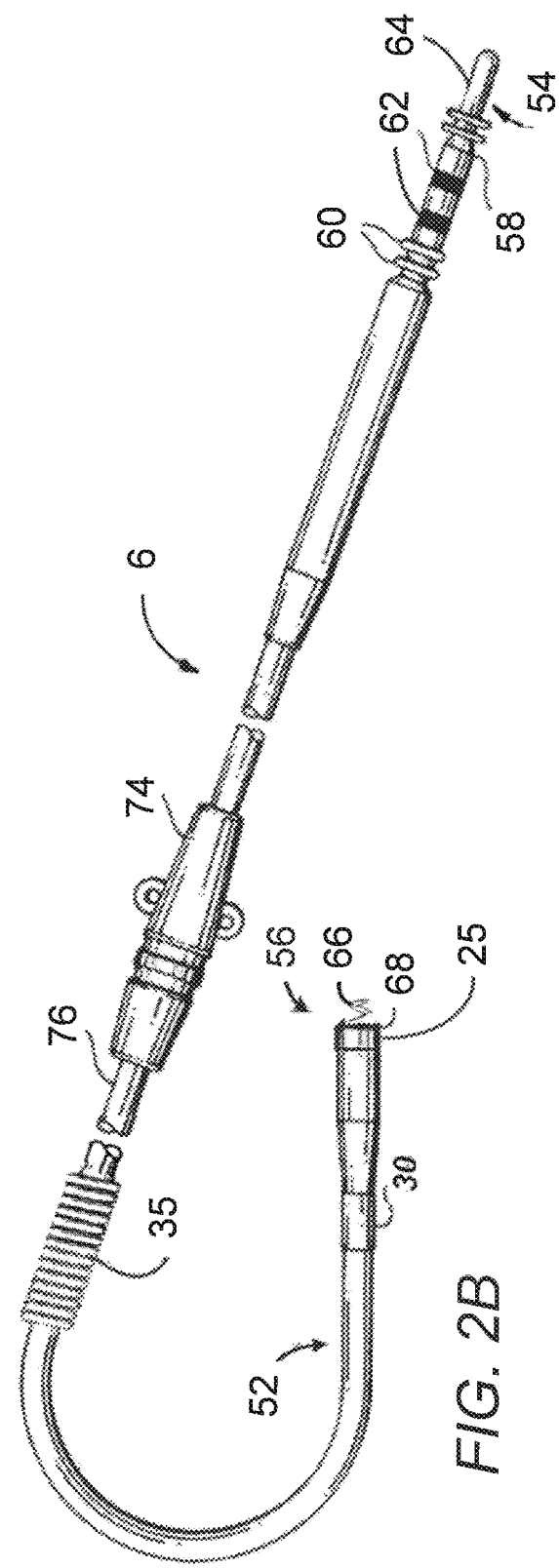
FIG. 2B is a plan view of a lead that is generally representative of any of the leads depicted in FIG. 2A and, more specifically, the RV lead.

FIG. 2B is a plan view of a lead that is generally representative of any of the leads 5, 6, 7 depicted in FIG. 2A and, more specifically, the RV lead 6. As can be understood from FIG. 2B, the lead 6 is designed for intravenous insertion and contact with the endocardium, and as such, may be conventionally referred to as an endocardial lead. As indicated in FIG. 2B, the lead 6 is provided with an elongated had body 52 that extends between a proximal region 54 and distal region 56 of the lead 6.

The proximal region 54 of the lead 6 includes a connector assembly 58, which is provided with sealing rings 60 and carries at least one or more electrical connectors in the form of ring contacts 62 and a pin contact 64.

As can be understood from FIGS. 2A and 2B, the connector assembly 58 is configured to be plugged into a receptacle of the pulse generator 20, the sealing rings 60 forming a fluid-tight seal to prevent the ingress of fluids into the receptacle of the pulse generator. When the connector assembly 58 is plugged into the pulse generator receptacle, the contacts 62, 64 electrically connect with the circuitry of the pulse generator 20 such that electrical signals can be administered and sensed by the pulse generator via the electrical pathways of the lead 6.

The connector assembly 58 is constructed using known techniques and is preferably fabricated of silicone rubber, polyurethane, silicone-rubber-polyurethane-copolymer ("SPC"), or other suitable polymer. The electrical contacts 62, 64 are preferably fabricated of stainless steel or other suitable electrically conductive material that is biocompatible.

As shown in FIG. 2B, the distal region 56 of the lead 6 includes a helical fixation anchor 66 distally extending from an extreme distal tip end 68 of the lead 6 when the helical fixation anchor 66 is in a deployed state. The helical fixation anchor 66 may be a tube-cut helical fixation anchor 66 and detailed specifics regarding the configuration and manufacture of the tube-cut helical fixation anchor 66 are provided below.

The anchor 66 may be active in that it can serve as an electrode in addition to serving as a mechanism by which the distal end of the lead can be affixed or anchored to endocardial tissue. Alternatively, the anchor 66 may be passive in that it simply serves an anchoring function while a tip electrode immediately proximally adjacent the anchor 66 contacts the endocardial tissue when anchored against such tissue by the anchor 66 being imbedded in the tissue. In some embodiments, the lead distal end is equipped with both an active anchor 66 and a tip electrode 25.

The tip electrode 25 and/or the active anchor 66 are electrically coupled to the pin contact 64 of the connector assembly 58 via electrical conductors extending through the lead body 62 in the form of wires, cables or other electrical conductors that are linear or helically coiled in configuration.

Depending on the embodiment, the anchor 66 may be transitioned to a non-deployed state via retraction of the anchor 66 into the confines of the distal region 56 of the lead 6. Alternatively, the anchor 66 may be transitioned to a non-deployed state via an obturator or other structural member being combined with the anchor 66 to inhibit the anchor 66 from being able to penetrate tissue. Finally, the anchor 66 may be transitioned to a non-deployed state by a sheath or other structure extending about and over the anchor 66 to cover the anchor and thereby inhibit the anchor 66 from being able to penetrate tissue.

As indicated in FIG. 2B, a ring electrode 30 may be located on the body 52 proximal the tip electrode 25 and anchor 66. The ring electrode 30 may fulfill both pacing and sensing duties. Where the lead 6 is equipped for defibrillation, the lead body 52 may also support one or more shock coils 35 located proximal the ring electrode 30. The shock coil 35 and ring electrode 30 are each respectively electrically coupled to one of the ring contacts 62 of the connector assembly 58 via electrical conductors extending through the lead body 62 in the form of wires, cables or other electrical conductors that are linear or helically coiled in configuration.

As indicated in FIG. 2B, the lead 10 may include a fixation sleeve 74 slidably mounted around the lead body 52 proximal the shock coil 35. The fixation sleeve 74 serves to stabilize the pacing lead 6 at the site of venous insertion.

The lead body 62 includes an outer insulation sheath 76 and an inner insulation sheath within the outer insulation sheath, the sheaths being arranged in concentric layers. The outer insulation sheath 76 is preferably fabricated of silicone rubber, polyurethane, silicone rubber-polyurethane-copolymer (SPC), or other suitable polymer. The inner insulation sheath may be formed of the same material as the outer insulation sheath or from another material such as, for example, polytetrafluoroethylene ("PTFE"). The insulation sheaths isolate the Interior components of the lead 6, including the electrical conductors from each other. The outer insulation sheath 76 isolates the inner components of the lead 6 from the surrounding environment and may be single or multi-layer construction.

The lead body 52 is constructed to include a hollow interior extending from the proximal region 54 to the distal region 56. The hollow interior allows for the introduction of a stylet, guidewire or other device during implant, which is beneficial in allowing the surgeon to guide the otherwise flexible lead 6 from the point of venous insertion to the myocardium.

b. Electrotherapy System Employing Leadless Pulse Generator

Figure 3A:
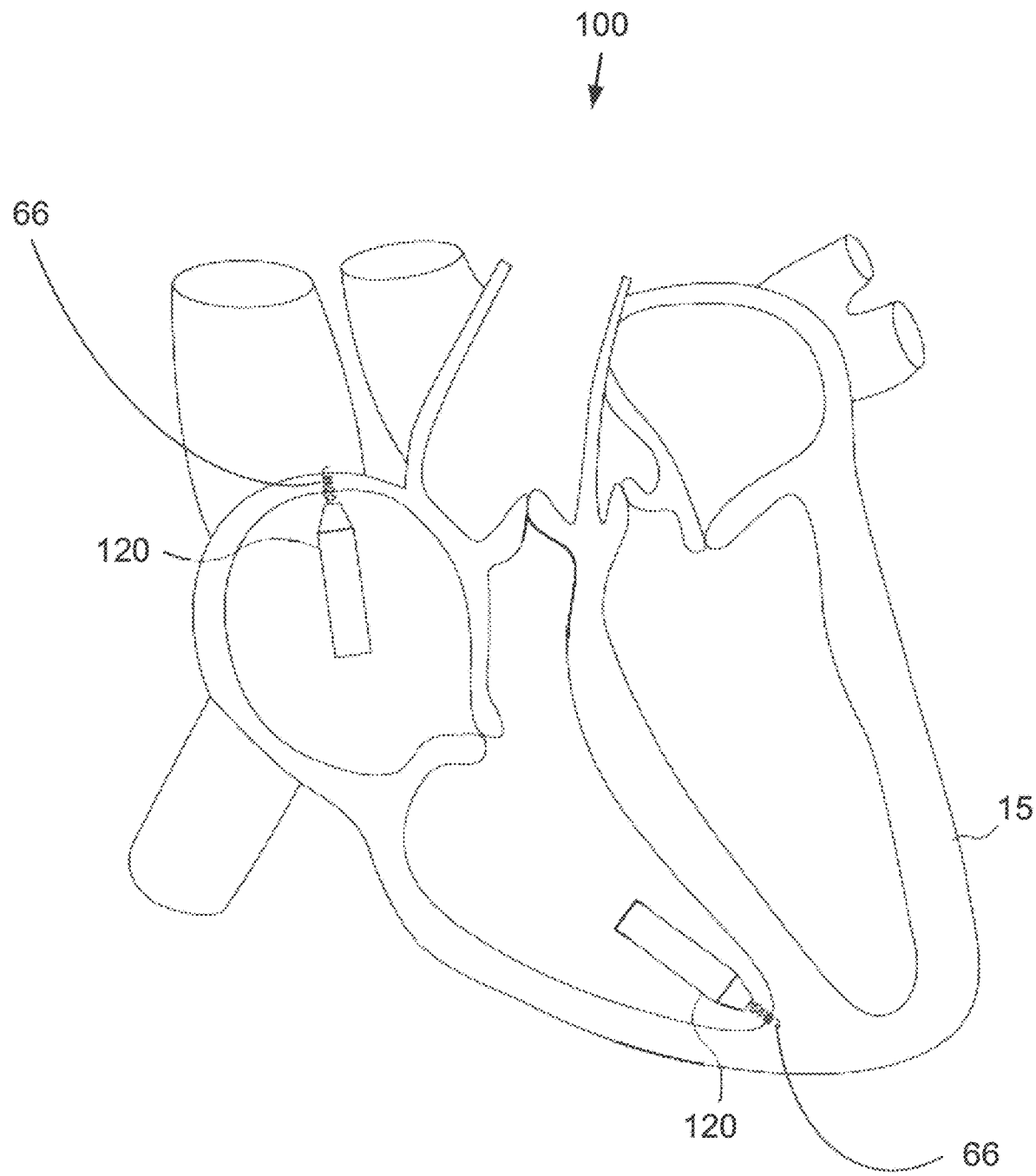
FIG. 3A is a diagrammatic depiction of a leadless electrotherapy system electrically coupled to a patient heart as viewed from an anterior side of the patient heart.

FIG. 3A is a diagrammatic depiction of a leadless electrotherapy system 100 electrically coupled to a patient heart 15 as viewed from an anterior side of the patient heart. The leadless electrotherapy system 100 employs one or more leadless pulse generators 120 (e.g., leadless pacemaker, leadless implantable cardioverter defibrillator (leadless-ICD), or etc.). As discussed in greater detail below, each leadless pulse generator 120 is substantially enclosed in a hermetic housing suitable for placement on or attachment to the inside or outside of a cardiac chamber. The leadless pulse generator can have two or more electrodes located within, on, or near the housing, for delivering pacing pulses to muscle of the cardiac chamber and optionally for sensing electrical activity from the muscle, and for bidirectional communication with at least one other device within or outside the body. The housing can contain a primary battery to provide power for pacing, sensing, and communication, for example bidirectional communication. The housing can optionally contain circuits for sensing cardiac activity from the electrodes. The housing contains circuits for receiving information from at least one other device via the electrodes and contains circuits for generating pacing pulses for delivery via the electrodes. The housing can optionally contain circuits for transmitting information to at least one other device via the electrodes and can optionally contain circuits for monitoring device health. The housing contains circuits for controlling these operations in a predetermined manner. In alternative embodiments, the housing may contain circuits for receiving and/or transmitting information via other communication means including, for example, Bluetooth, etc.

In some embodiments, a leadless pulse generator 120 can be adapted for implantation into tissue in the human body. In a particular embodiment, a leadless cardiac pacemaker can be adapted for implantation adjacent to heart tissue on the inside or outside wall of a cardiac chamber, using two or more electrodes located on or within the housing of the pacemaker, for pacing the cardiac chamber upon receiving a triggering signal from at least one other device within the body.

Self-contained or leadless pulse generators are typically fixed to an intracardiac implant site by an actively engaging mechanism such as a screw or helical member that screws into the myocardium. Examples of such leadless pulse generators are described in the following publications, the disclosures of which are incorporated by reference in their respective entireties herein: (1) U.S. application Ser. No. 11/549,599, filed on Oct. 13, 2006, entitled "Leadless Cardiac Pacemaker System for Usage in Combination with an Implantable Cardioverter-Defibrillator", and published as US2007/0088394A1 on Apr. 19, 2007; (2) U.S. application Ser. No. 11/549,581 filed on Oct. 13, 2006, entitled "Leadless Cardiac Pacemaker", and published as US2007/0088396A1 on Apr. 19, 2007; (3) U.S. application Ser. No. 11/549,591, filed on Oct. 13, 2006, entitled "Leadless Cardiac Pacemaker System with Conductive Communication" and published as US2007/0088397A1 on Apr. 19, 2007; (4) U.S. application Ser. No. 11/549,596 filed on Oct. 13, 2006, entitled "Leadless Cardiac Pacemaker Triggered by Conductive Communication" and published as U52007/0088398A1 on Apr. 19, 2007; (5) U.S. application Ser. No. 11/549,603 filed on Oct. 13, 2006, entitled "Rate Responsive Leadless Cardiac Pacemaker" and published as US2007/0088400A1 on Apr. 19, 2007: (6) U.S. application Ser. No. 11/549,605 filed on Oct. 13, 2006, entitled "Programmer for Biostimulator System" and published as US2007/0088405A1 on Apr. 19, 2007; (7) U.S. application Ser. No. 11/549,574, filed on Oct. 13, 2006, entitled "Delivery System for Implantable Biostimulator" and published as U52007/0088418A1 on Apr. 19, 2007; and (8) International Application No. PCT/US2006/040564, filed on Oct. 13, 2006, entitled "Leadless Cardiac Pacemaker and System" and published as WO07047681A2 on Apr. 26, 2007.

Figure 3B:
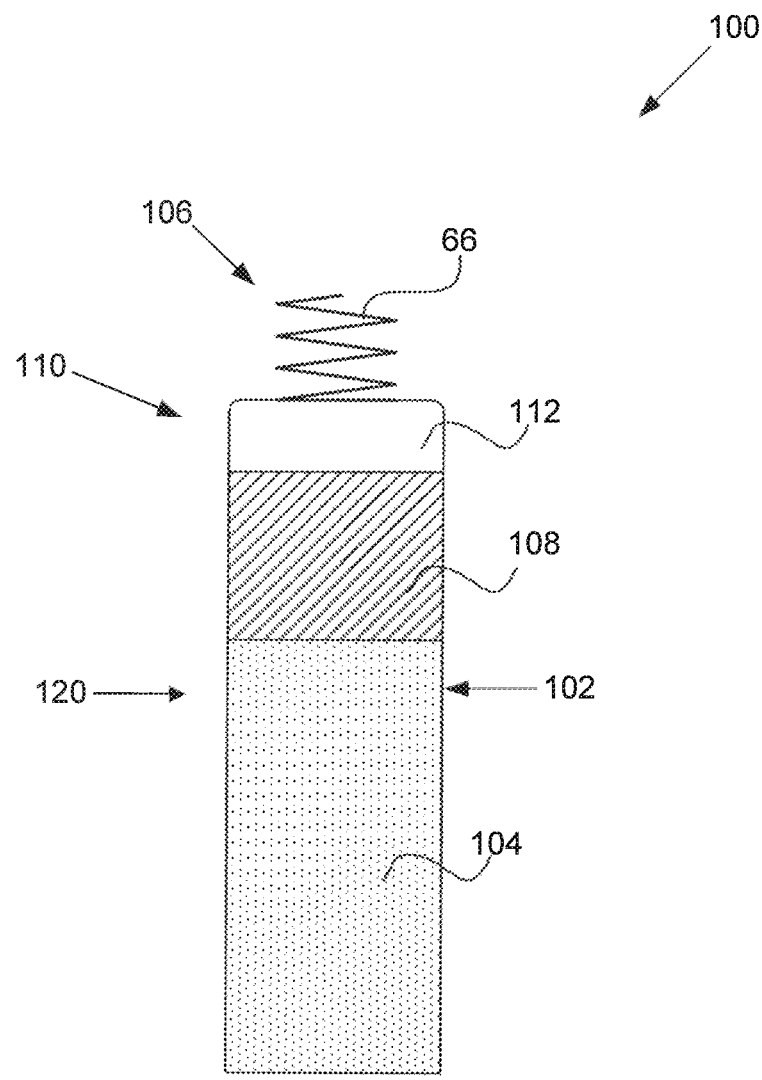
FIG. 3B is a plan view of a leadless pacemaker or biostimulator that is generally representative of any of the leadless pacemakers or biostimulators depicted in FIG. 3A.

FIG. 3B depicts a leadless pulse generator 120. The leadless pulse generator can include a hermetic housing 102 with electrodes 104 and 106 disposed thereon. As shown, electrode 106 can be disposed on or integrated within a helical fixation anchor 66, and the electrode 104 can be disposed on the housing 102. As discussed in greater detail below, the helical fixation anchor 66 can be a tube-cut helical fixation anchor 66 for attaching the housing to tissue, such as heart tissue. In other embodiments, the electrode 106 may be independent from the helical fixation anchor 106 in various forms and sizes. The housing can also include an electronics compartment 110 within the housing that contains the electronic components necessary for operation of the pulse generator. The hermetic housing can be adapted to be implanted on or in a human heart, and can be cylindrically shaped, rectangular, spherical, or any other appropriate shapes, for example.

The housing can comprise a conductive, biocompatible, inert, and anodically safe material such as titanium, 316L stainless steel, or other similar materials. The housing can further comprise an insulator disposed on the conductive material to separate electrodes 104 and 106. The insulator can be an insulative coating on a portion of the housing between the electrodes, and can comprise materials such as silicone, polyurethane, parylene, or another biocompatible electrical insulator commonly used for implantable medical devices. In the embodiment of FIG. 3B, a single insulator 108 is disposed along the portion of the housing between electrodes 104 and 106. In some embodiments, the housing itself can comprise an insulator instead of a conductor, such as an alumina ceramic or other similar materials, and the electrodes can be disposed upon the housing.

As shown in FIG. 3B, the biostimulator can further include a header assembly 112 to isolate electrode 104 from electrode 106. The header assembly 112 can be made from tecothane or another biocompatible plastic, and can contain a ceramic to metal feedthrough, a glass to metal feedthrough, or other appropriate feedthrough insulator as known in the art.

The electrodes 104 and 106 can comprise pace/sense electrodes, or return electrodes. A low-polarization coating can be applied to the electrodes, such as platinum, platinum-iridium, iridium, iridium-oxide, titanium-nitride, carbon, or other materials commonly used to reduce polarization effects, for example. In FIG. 3B, electrode 106 can be a pace/sense electrode and electrode 104 can be a return electrode. The electrode 104 can be a portion of the conductive housing 102 that does not include an insulator 108.

Figure 4:
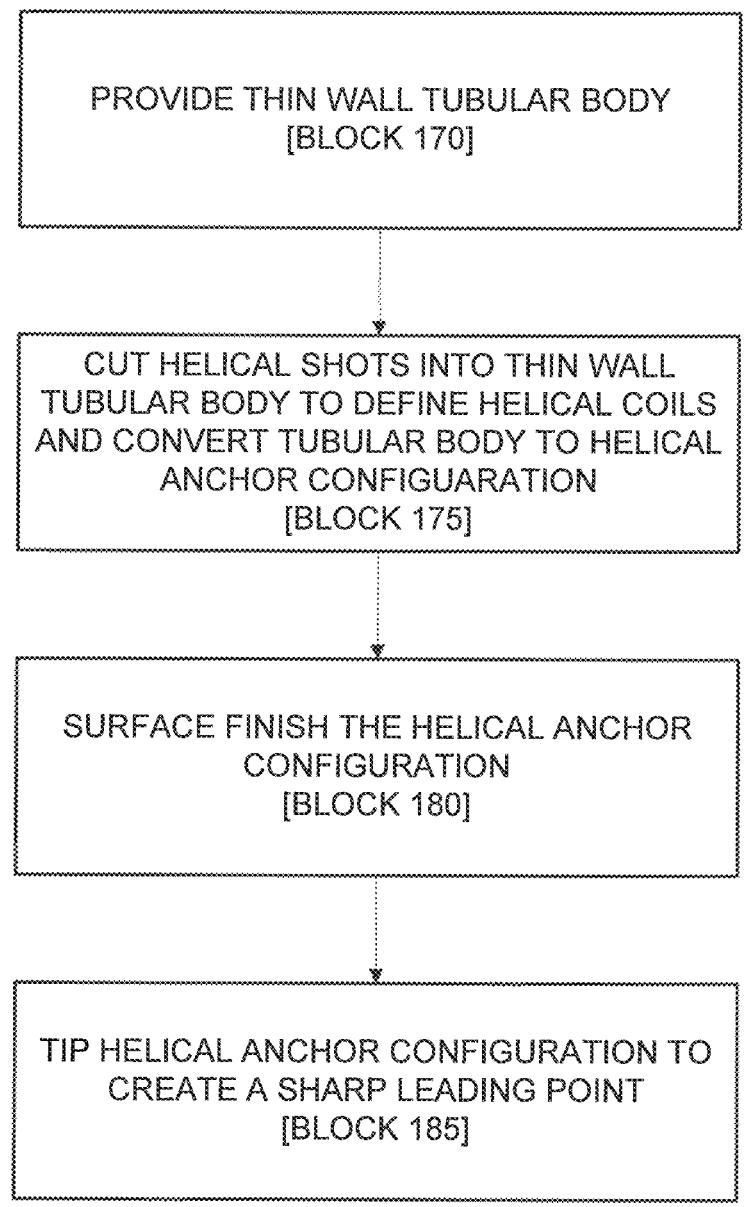
FIG. 4 outlines a method of manufacturing a tube-cut helical fixation anchor from a thin walled tubular body.
Figure 5:
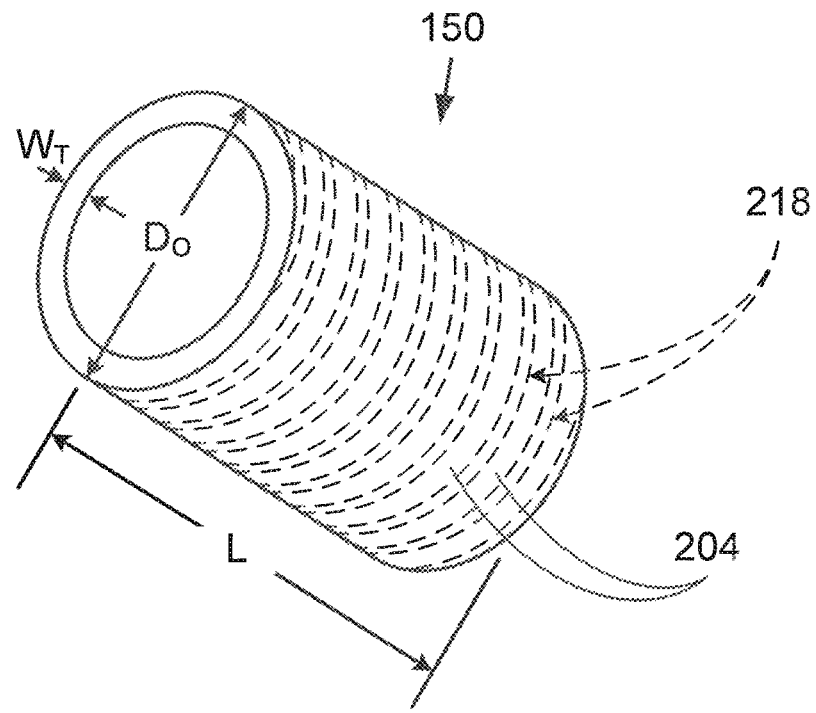
FIG. 5 is an isometric view of the tubular body used to manufacture the tube-cut helical fixation anchor.

Several techniques and structures can be used for attaching the housing 102 to the interior or exterior wall of the heart as depicted in FIG. 3A. A helical fixation anchor 66, can enable insertion of the device endocardially or epicardially through a guiding catheter. A torqueable catheter can be used to rotate the housing and force the helical fixation anchor 66 into heart tissue, thus affixing the fixation anchor (and also the electrode 106 in FIG. 3A) into contact with stimulable tissue, as illustrated in FIG. 3A. Electrode 104 can serve as an indifferent electrode for sensing and pacing. The fixation anchor may be coated partially or in full for electrical insulation, and a steroid-eluting matrix may be included on or near the device to minimize fibrotic reaction, as is known in conventional pacing electrode-leads. The tube-cut helical fixation anchor 66 may be fixed or extendable/retractable relative to the distal end of the leadless puke generator 120.

c. Tube-Cut Helical Fixation Anchor For Use On Implantable Medical Leads And Leadless Pulse Generators As already mentioned above, the implantable medical leads or leadless pulse generators disclosed herein may employ a tube-cut helical fixation anchor 66 for actively fixating the implantable device to cardiac tissue. A method of manufacturing the tube-cut anchor 66 is outlined in FIG. 4, and as reflected there, a tubular body 150 is provided [block 170]. As indicated in FIG. 5, which is an isometric view of the tubular body 150, in one embodiment, the tubular body is a thin wailed cylindrical body 150 having an outer diameter $D_o$ of between approximately 0.02" and approximately 0.5", a wall thickness $W_T$ of between approximately 0.005" and approximately 0.10", and an overall length L of between approximately 0.02" and approximately 1". The tubular body 150 may be formed of: stainless steel; Nitinol; cobalt alloys such as MP35N and 35N-LT; various platinum alloys such as Ptlr and PTW; polymers such as Peek, nylon, glass filled nylon, etc. In other embodiments, the tubular body 150 may be similar to the thin wall body depicted in FIG. 5, except having a shape other than cylindrical, such as, for example, square, hexagonal, octagonal, etc.

The geometry of the tube-cult helical anchor 66 may be designed in CAD and a manufacturing file can be generated and sent to a manufacturing device. As can be understood from FIG. 5, the manufacturing device cuts helical slots 218 in the tubular body 150 to define the helical turns 204 of the tube-cut helical anchor 66 into the tubular body [block 175]. The manufacturing device may employ any appropriate mechanical, energy or chemical cutting method to define the helical cuts 218 into the tubular body 150. For example, one embodiment may employ laser cutting. Other cutting methods may include water jet, plasma, and other cutting methods known in the art. Further treatments used to result in a production ready tube-cut helical anchor 66 include surface finishing [block 180] and tipping [block 185]. Surface finishing may include, for example, pickling, passivation, and electropolishing. Tipping to create a sharp leading point may be performed via, for example, using a combination of CNC grinding and electropolishing.

Figure 6:
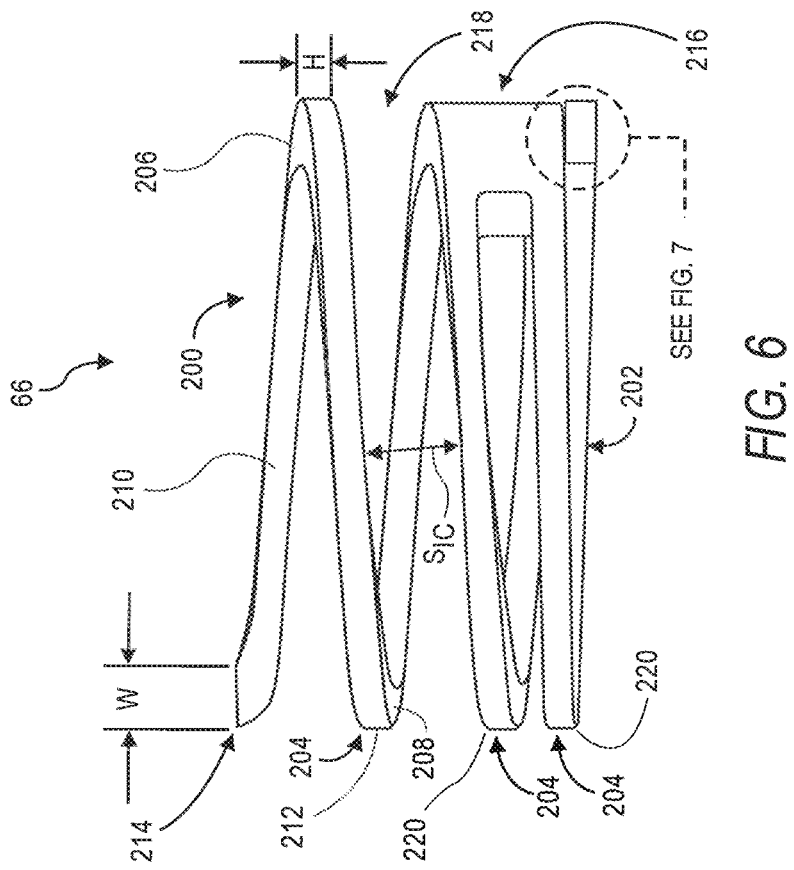
FIG. 6 is a side elevation of a first embodiment of the tube-cut helical fixation anchor.
Figure 7:
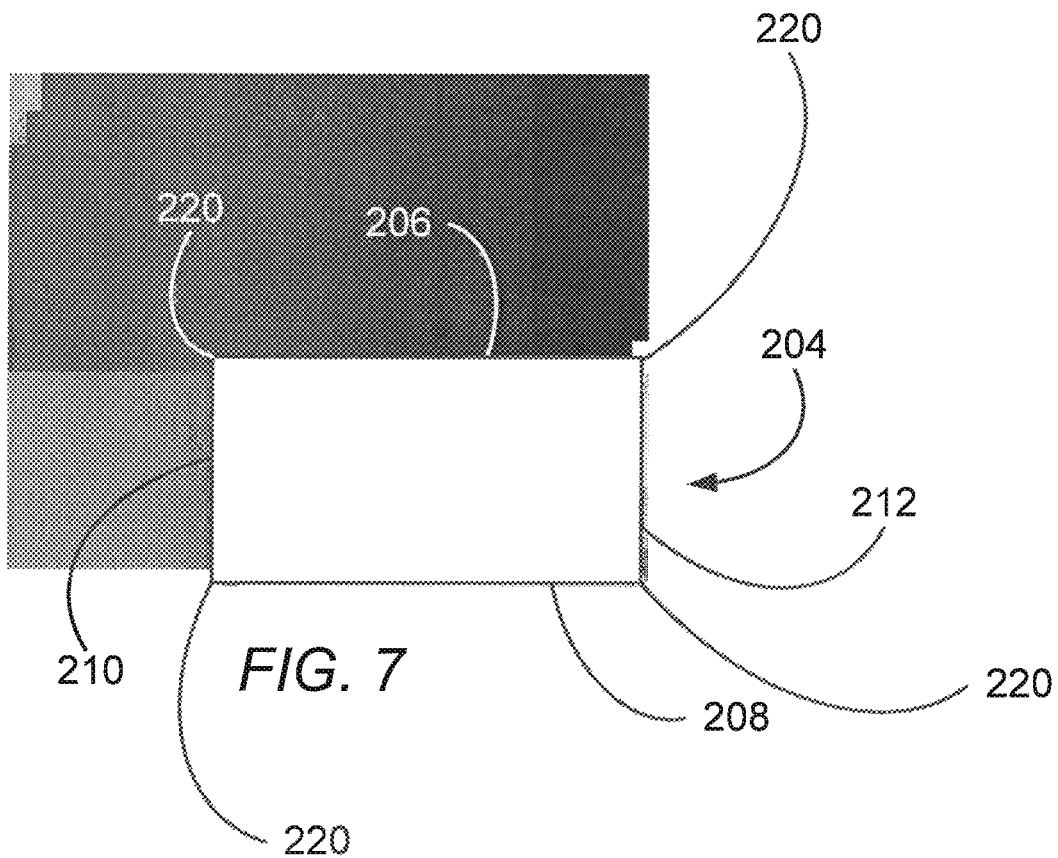
FIG. 7 is an enlarged view of the proximal termination of the most proximal helical turn of the tube-cut helical fixation anchor of FIG. 6 and illustrates the quadrilateral cross-section of the most proximal helical turn as defined by the four surfaces of the most proximal helical turn.

To begin a discussion regarding the structural details of the tube-cut helical fixation anchor 66 disclosed herein, reference is made to FIG. 6, which is a side elevation of a first embodiment of the tube-cut anchor 66. As shown in FIG. 6, the tube-cut anchor 66 includes a distal end 200, a proximal end 202, and helical turns 204 extending between the distal and proximal ends. Each helical turn 204 includes a helically sloped flat distal surface 206, a helically sloped flat proximal surface 208 opposite the helically sloped flat distal surface, an arcuate radially inward surface 210, and an arcuate radially outward surface 212 opposite the arcuate radially inward surface. As can be understood from FIG. 7, which is an enlarged view of the proximal termination of the most proximal helical turn of the tube-cut anchor of FIG. 6, these four surfaces 206, 208, 210, 212 define a quadrilateral cross-section, which is representative of the cross-section of each of the helical turns 204 making up the tube-cut anchor 66. Specifically, for a cross-section of a turn 204, which would appear similar to the proximal turn termination shown in FIG. 7, the distal and proximal surfaces 206, 208 define a first pair of spaced-apart parallel boundary ones which are perpendicular to another pair of space-apart parallel boundary lines defined by the arcuate radially inward and outward surfaces 210, 212. The quadrilateral cross-section may be rectangular, as indicated in FIG. 7, or even square. Each perpendicular intersection between the surfaces 206, 208, 210, 212 define perpendicular or acute edges 220 that extend along the length of the helically extending turns 204 forming the tube-cut helical fixation anchor 66.

In contrast to the round cross-section of the prior art wound-wire, helical fixation anchor 1 of FIG. 1, cutting a helical fixation anchor 66 out of a cylindrical tube 150 results in the tube-cut helical fixation anchor 66 having helical turns 204 with quadrilateral cross-sections. Holding material property and number of windings at a constant, the stiffness of a helical fixation anchor is dictated by the geometry of its cross-section. For example, the prior art wound-wire helical fixation anchor 1 of FIG. 1 may be made of a round wire 2 with a diameter $D_{IA}$ of 0.015", yet this prior art anchor 1 may be less rigid than the tube-cut helical fixation anchor 66 of FIG. 6, which may have a 0.008"H× 0.030"W quadrilateral cross-section. Thus, although the height H of each helical turn 204 of the tube-cut anchor 66 is nearly half of the height (i.e., diameter $D_{IA}$) of the helical turn of the wound-wire anchor 1, the tube-cut anchor 66 ends up being more rigid than the wound-wire anchor 1. This phenomenon is the result of the moment of inertia of the cross-section. In lay terms, the aspect ratio of width to height of a quadrilateral changes the susceptibility of bending. Since the width and height of the quadrilateral cross-sections of the helical turns comprising the tube-cut anchor can be selected independently, these dimensions—and thus this aspect ratio—can be selected to achieve specific or advantageous mechanical and/or physical capabilities. There is no ability to vary this aspect ratio in a round wire (its aspect ratio is always equal to one), and the only dimensional means to increase its rigidity is to increase the total diameter of the wire, which is disadvantageous.

As can be understood from a side-by-side comparison of the exemplary anchors of FIGS. 1 and 6, the tube-cut anchor 66 of FIG. 6 is a low profile helix with turns 204 of low cross-sectional height H despite having a width of 0.030" that is twice the diameter $D_{IA}$ of 0.015" of the round wire 2. In this example, the difference in height of the helix cross-section [i.e., 0.015" (round of FIG. 1) vs 0.008 (quadrilateral of FIG. 6)] offers the opportunity to overcome the challenges mentioned above. Specifically, the low cross-sectional height H of the helical turns 204 of the tube-cut anchor 66 allows for a helix of small pitch (i.e., the helical turns 204 have a small incline) while providing an inter-turn space $S_{IC}$ (i.e., the open space between adjacent helical turns) that exceeds the inter-turn space $S_{IC}$ offered by round wire helical turns 1 of similar or even slightly greater pitch. This small pitch or small incline resulting from the lower cross-sectional height H allows for a better chance that the tube-cut helical fixation anchor 66 remains in tissue while reducing the likelihood of penetrating through or protruding beyond the engaged tissue thickness or cutting or pinching the tissue due to overly narrow inter-turn space $S_{IC}$. Also, the small pitch or small incline of the turns 204 of the low profile helix allows for a shallow introduction into the target implant tissue. Furthermore, the small pitch or small incline that results from the lower cross-sectional height H allows for the tube-cut helical fixation anchor 66 to be more in plane/flush with the tissue. As a result, if the tube-cut helical fixation anchor 66 were to protrude out of the tissue, the flush tube-cut helical fixation anchor 66 is less likely to irritate or attach to the pericardium as compared to the round cross-sectional wire of the prior art anchor 1 of FIG. 1.

Further advantages are also provided by the fact that the tube-cut anchor 66 offers a lower turn height H as compared to the round wire 2 of the prior art anchor 1 of FIG. 1 while still providing substantial rigidity. For example, as can be understood from FIG. 1, if the turns of the wound-wire helical anchor 1 were formed of wire 2 having a diameter $D_{IA}$ of 0.015" and the tube-cut anchor 66 had turns 204 with a turn cross-section having a turn height H of 0.008" and a turn width W of 0.03", the wound-wire helical anchor 1 and the tube-cut anchor 66 would have equivalent rigidities, despite the turn height H of the tube-cut anchor 66 being approximately half of the turn height (i.e., wire diameter $D_{IA}$) of the wound-wire helical anchor 1. As readily understandable from a comparison of FIGS. 1 and 6, the smaller turn height H of the tube-cut anchor 66 allows for substantially greater inter-turn space $S_{IC}$ as compared to that of the wound-wire helical anchor 1 while still providing equivalent rigidity.

The low helix cross-section height H of 0.008" of each turn 204 of the tube-cut helical fixation anchor 66 of FIG. 6 allows for more windings in the same overall height of the anchor 66, thereby allowing for more turns into the tissue as compared to the prior art wound-wire helical fixation anchor 1. The greater the number of turns, the more anchor-tissue engagement, thus decreasing the likelihood of dislodgement.

The quadrilateral cross-section of turns 204 of the tube-cut helical fixation anchor 66 of FIG. 6 can allow for a better bad distribution versus the round wire 2 of the prior art wound-wire helical fixation anchor 1 of FIG. 1. For instance, in the above example, the bad would be supported by flat surfaces 206, 208 having a width W of 0.030" in the tube-cut anchor 66 of FIG. 6 versus a 0.015" $D_{IA}$ (i.e., wide) circular surface of the prior art wound-wire anchor 1 of FIG. 1. Moreover, the circular shape of the prior art wound-wire anchor 1 of FIG. 1 results in a focal high pressure point between adjacent winds of the prior art wound-wire helical fixation anchor 1.

When forming the prior art wound-wire helical fixation anchor 1 of FIG. 1 out of wire, the manufacturing process is effectively wire bending. In contrast, forming the tube-cut helical fixation anchor 66 of FIG. 6 out of a thin-walled tubular body 150 provides much more material for manipulation and is a material removal process. This process is advantageous over that of the prior art anchor for a number of reasons, including, for example, the ability to alter the amount and shape of the material removed to result in varying cross-sections and nonlinear helical paths. Also, anti-rotation features can be created and configured to prevent dislodgement. Such anti-rotation features may include, for example, barbs, serpentine sections that retain tissue without injury, or etc. These advantageous features are discussed in detail below with respect to FIGS. 10-13.

Returning to the discussion of the details of the tube-cut anchor 66 of FIG. 6, the distal termination of the most distal helical turn of the tube-cut anchor 66 terminates as a distal tip 214, wherein the distal tip is sharpened or tapered to facilitate the distal tip 214 being able to pierce cardiac tissue. The distal tip may be the result of one, two, three or more facet grinds. The extreme point termination of the distal tip 214 may be located at a variety of positions such as, for example at the distal limit of intersection of planes 206 and 212, the intersection of planes 206 and 210, the intersection of planes 208 and 212, or the intersection of planes 208 and 210. Alternatively, the extreme point termination of the distal tip 214 may be centered side-to-side and top-to-bottom relative to planes 206, 208, 210, or 212, or the extreme point termination of the distal tip 214 may terminate centered on any of the planes 206, 208, 210, or 212. Of course other point termination configurations are possible and contemplated.

As indicated in FIG. 6, the helical winding of the helical turns 204 is generally continuous and uninterrupted except in a region 216 near the proximal end 202 wherein two adjacent turns 204 are joined together by a continuous cylindrical wall portion 216 wherein the material forming the cylindrical tube 150 of FIG. 5 from which the anchor 66 was cut was not removed from between the adjacent turns 204. In other words, the helical gap 218 that was cut into the cylindrical tube 150 of FIG. 5 to define the turns 204 of the anchor 66 does not extend through the cylindrical wall portion 216. This continuous cylindrical wall portion 216 provides a rigid structure by which the anchor 66 can be solidly coupled to the supporting device, whether that device is the above-described leadless pulse generator 120 described with respect to FIG. 3B or the above-described implantable medical lead 6 described with respect to FIG. 2B.

In other words, the tube-cut helical anchor 66 can be formed with an integrated tubular base section 216. The base section 216 can be created to assist in assembling and securing the tube-cut helical anchor 66 to the body of the device, whether that device is a leadless pacer or an implantable medical lead. This base section 216 of the tube-cut anchor 66 is a significant advantage over the prior art wound-wire anchor 1 of FIG. 1 because a wound-wire anchor 1 typically requires a second part to secure the wound-wire anchor to a device sufficiently to allow for reliable turning into tissue.

As can be understood from FIG. 6, in one embodiment, each turn 204 has a transverse width W of 0.02" and a proximal-distal H of 0.01". In another embodiment, each turn 204 has a transverse width W of 0.03" and a proximal-distal H of 0.008". In yet other embodiments, each turn 204 has a transverse width W of between approximately 0.006" and approximately 0.1" and a proximal-distal H of between approximately 0.003" and approximately 0.05". In one embodiment, the turns 204 may have a helical pitch of between approximately 0.01" and approximately 0.1".

Figure 8:
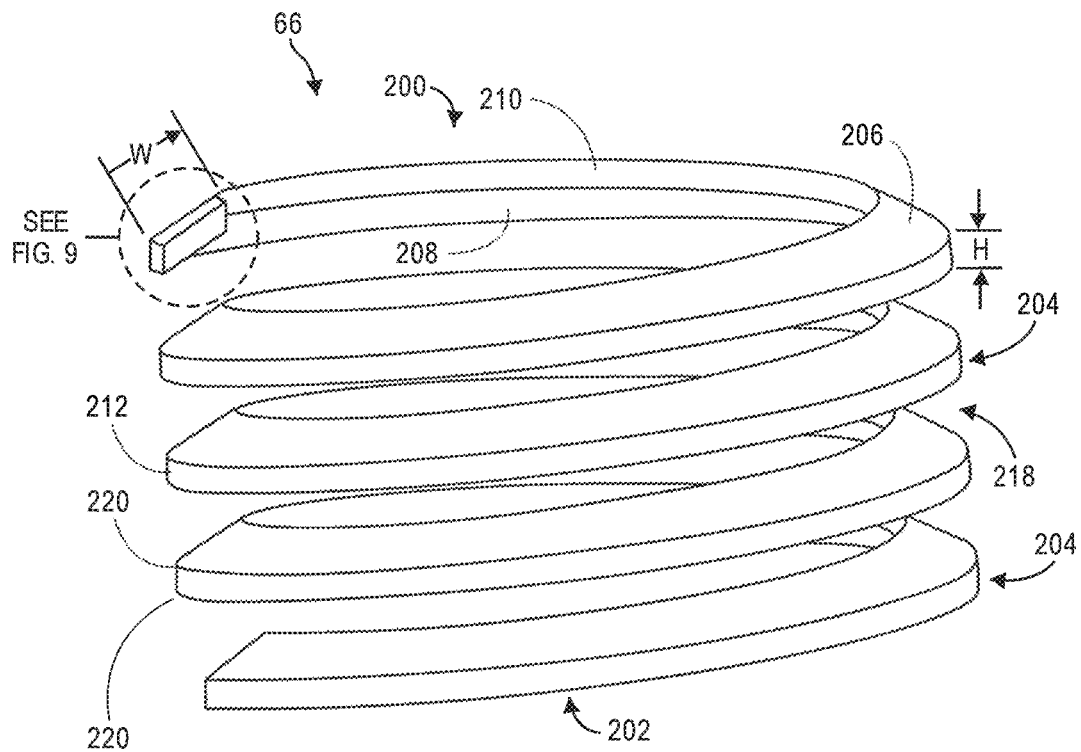
FIG. 8 is side elevation of an embodiment of the tube-cut helical fixation anchor having an angled quadrilateral cross-section.

FIG. 8 is side elevation of an embodiment of the tube-cut helical fixation anchor 66 having an angled quadrilateral cross-section. It should be noted that the anchor 66 depicted in FIG. 8 is not yet complete as it does not yet include a base section and the distal tip 214 has not yet been sharpened into a sharpened tip. As can be understood from FIG. 8, the slots or gaps 218 have been cut into the cylindrical tubular body 150 (shown in FIG. 5) at an angle relative to the longitudinal center axis of the tubular body 150. As a result, and as shown in FIG. 8, the distal and proximal surfaces 206, 208 of each turn 204 of the tube-cut helical anchor 66 are also oblique relative to the center longitudinal axis of the anchor 66. As can be understood from FIG. 9, which is an enlarged view of a region surrounding the distal termination of the tube-cult helical anchor 66 of FIG. 8 prior to being sharpened into a distal tip 214, each turn 240 has an angled quadrilateral cross-section or, in other words, may be shaped as a parallelogram with unequal pairs of corner angles such that two of the intersecting edges 220 have equal obtuse angles and the other two intersecting edges 220 have equal acute angles.

Figure 9:
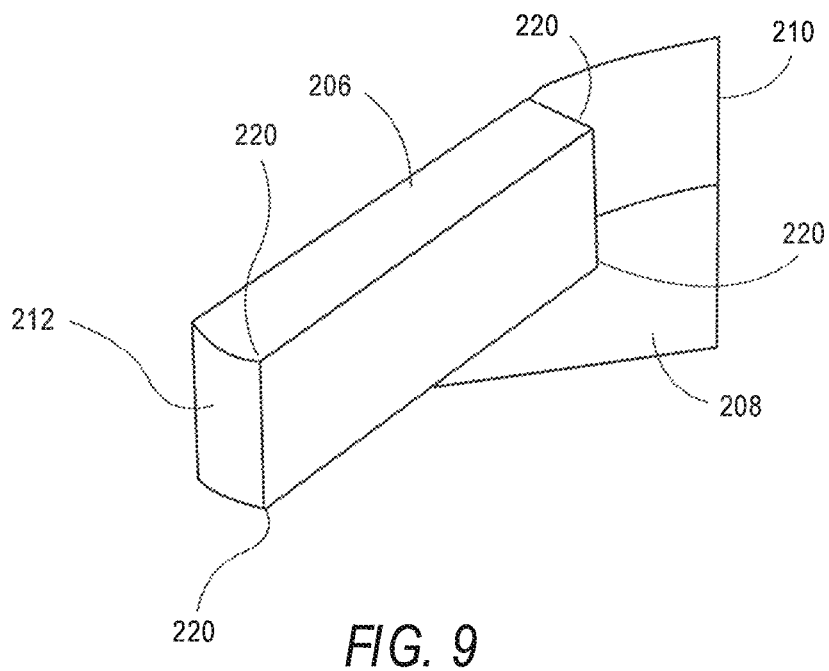
FIG. 9 is an enlarged view of a region surrounding the distal termination of the tube-cut helical anchor of FIG. 8 prior to the distal termination being sharpened into a distal tip.

In addition to the height H and width W of the turns of the anchor 66, the angle at which the quadrilateral is cut relative to the central longitudinal axis of the tube-cut helical anchor 66 provides yet another parameter that can be modified to enhance the overall performance and functionality of the anchor 66. For example, a tube-cut helical anchor 66 using an angled quadrilateral ab depicted in FIG. 8 will be more resistant to bending/flexing than an equivalent helical anchor 66 using a non-angled quadrilateral. Accordingly, the height of the angled quadrilateral could be reduced and still achieve the same target stiffness, therein enabling further reductions in helix pitch that would provide for opportunities to increase the number of helix turns for a given helix height or further reduce overall helix height for a given number of helix turns. While FIGS. 8 and 9 illustrate an embodiment including helical turns 204 with a "downward-angled" quadrilateral cross-section, a similar helical arrangement with an "upward-angled" quadrilateral cross-section is formed in other embodiments.

As can be understood from FIG. 8, the leading edge of the distal tip 214 is defined in the internal diameter (i.e., at the inner arcuate surface 210 of the distal termination of the most distal turn 204 of the tube-cut helical anchor 66). Such an arrangement of the leading edge of the distal tip 214 helps to keep the leading edge away from the vessel wall as the device is being tracked through the patient vasculature during implantation of the device. In other embodiments, the distal tip may be oppositely configured in that the leading edge of the distal tip 214 is defined in the outer diameter (i.e., at the outer arcuate surface 212 of the distal termination of the most distal turn 204 of the tube-cut helical anchor 66).

Figure 10:
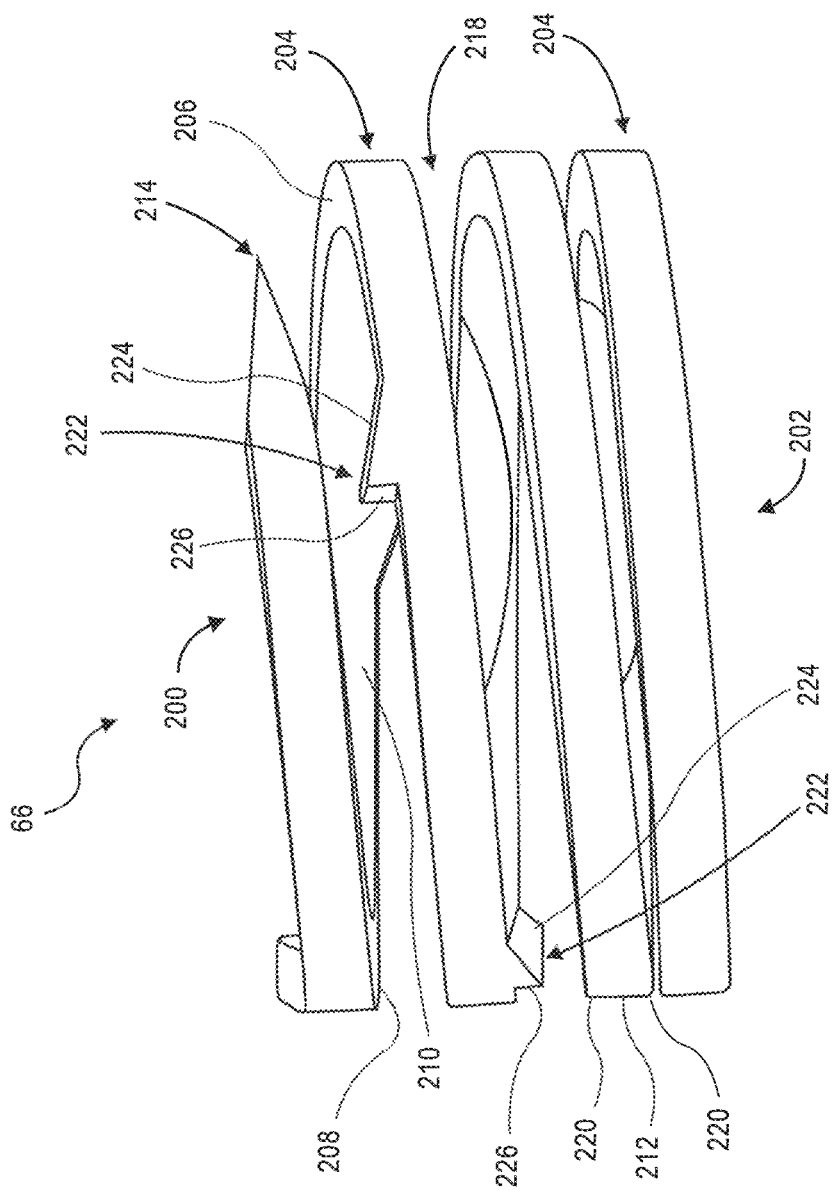
FIG. 10 is a side elevation of an embodiment the tube-cut helical fixation anchor having turns configured for anti-rotation, one or more barbs being defined in the distal and proximal surfaces of one or more turns of the tube-cut helical fixation anchor.

As mentioned above, because the tube-cut helical fixation anchor 66 is formed via cutting or material removal process that provides the ability to alter the amount and shape of the material removed, the resulting turns 204 of the anchors 66 can have a variety of cross-sections, nonlinear helical paths, and anti-rotation features that can be created and configured to prevent dislodgement. For example, as shown in FIG. 10, which is a side elevation of an embodiment the tube-cut helical fixation anchor 66 having turns configured for anti-rotation, one or more barbs 222 may be defined in the distal and proximal surfaces 206, 208 of one or more turns 204 of the anchor 66. Such barbs 222 may have a leading surface 224 and a trailing surface 226 with asymmetrical slopes, with the slope of the leading surface 224 generally being shallower than that of the trailing surface 226. For example, such barbs 222 may have a sloped leading surface 224 and a perpendicular or acute trailing surface 226. The sloped leading surface 224 forms an obtuse angle with its supporting surface 206, 208 such the tissue can readily slide up its gradual slope to pass over to the trailing surface 226 when the anchor 66 is being screwed into tissue. The trailing surface 226, which forms a perpendicular or acute angle with its supporting surface 206, 208, inhibits the tissue from easily reversing course relative to the barb 222 should an unscrewing force be applied to the anchor 66. It is impossible to achieve this barbed helical flat turn geometry using round wire. The barbed configuration allows for forward rotation and resists backward rotation, thereby mitigating device dislodgement.

Figure 11:
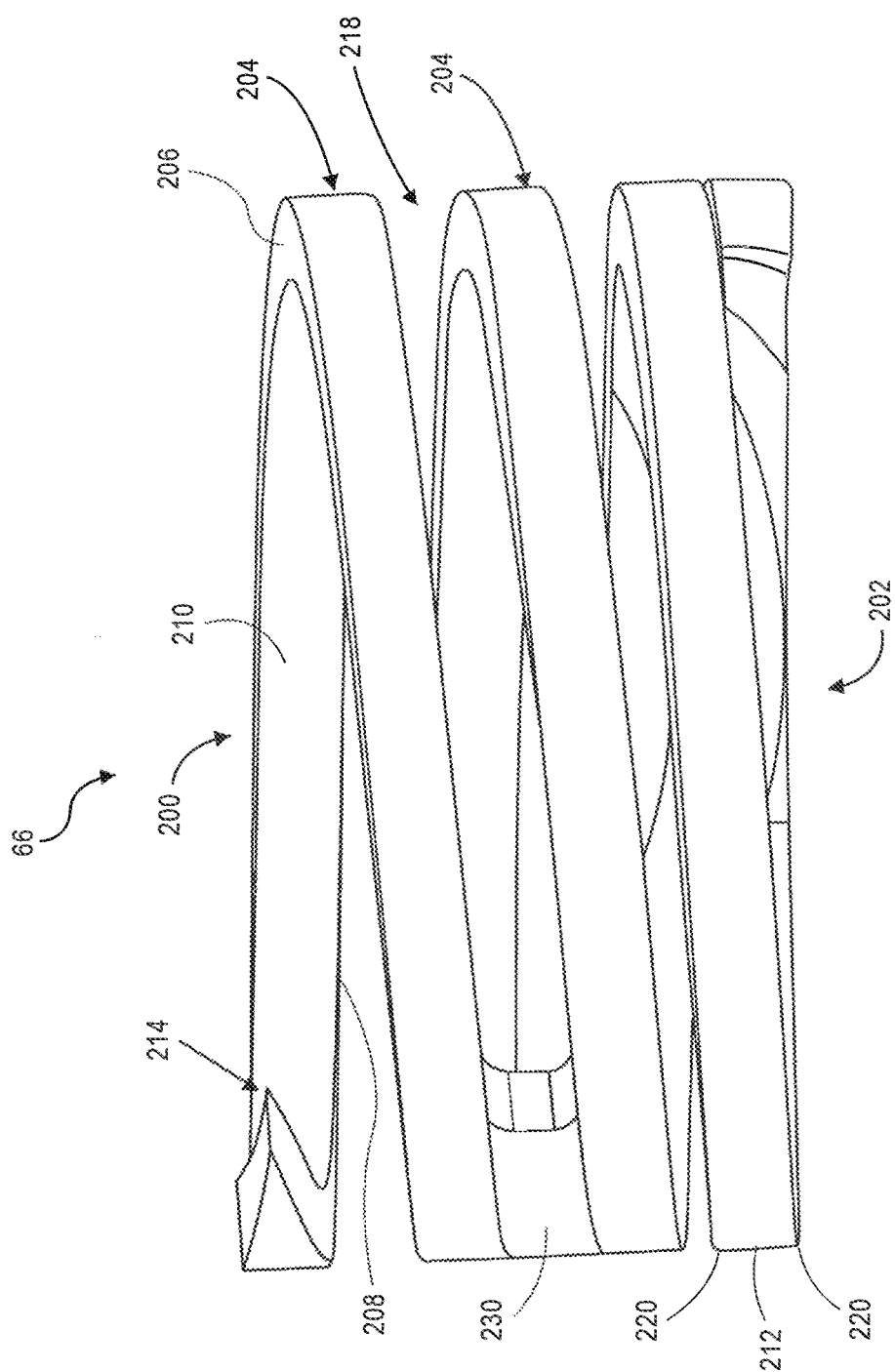
FIG. 11 is a side elevation of an embodiment of the tube-cut helical fixation anchor employing an occlusion or inter-turn structural enhancement that can be used as a stop to prevent collapse of the helical arrangement of the anchor and/or to prevent further penetration of the anchor into the tissue (i.e., define a maximal number of penetrating rotations of the anchor into the tissue), thereby acting as a tissue stop to avoid excessive compression of the tissue.

FIG. 11 is a side elevation of an embodiment of the tube-cut helical fixation anchor 66 employing an occlusion or inter-turn structural enhancement 230 that can be used as a stop to prevent collapse of the helical arrangement of the anchor 66. Collapse of the helical configuration of an anchor can result in tissue being pinched between the turns of the anchor and occasionally occurs via the application of forward pressure to the anchor during implantation of a device on which the anchor is supported, such anchor collapse also preventing tissue engagement. Also, the occlusion 230 creates a functional stop that prevents further rotation/penetration of the tube-cut helical fixation anchor 66 into the tissue without pinching the tissue at that stopping point. As shown in FIG. 11, the occlusion 230 extends between adjacent turns 204.

As indicated in FIG. 11, the hellcat winding of the helical turns 204 is generally continuous and uninterrupted except in a region 230 near intermediate the distal and proximal ends 200, 202 wherein two adjacent turns 204 are joined together by a continuous cylindrical wall portion 230 wherein the material forming the cylindrical tube 150 of FIG. 5 from which the anchor 66 was cut was not removed from between the adjacent turns 204. In other words, the helical gap 218 that was cut into the cylindrical tube 150 of FIG. 5 to define the turns 204 of the anchor 66 does not extend through the cylindrical wall portion 230. This continuous cylindrical wall portion 230 provides a rigid structure between adjacent turns 204, intermediate the length of the anchor 66. This rigid structure helps to structurally reinforce the anchor 66 to reduce the chances of anchor collapse and also provides a functional stop that prevents further rotation/penetration of the tube-cut helical fixation anchor 66 into the tissue without pinching the tissue at that stopping point.

Figure 12:
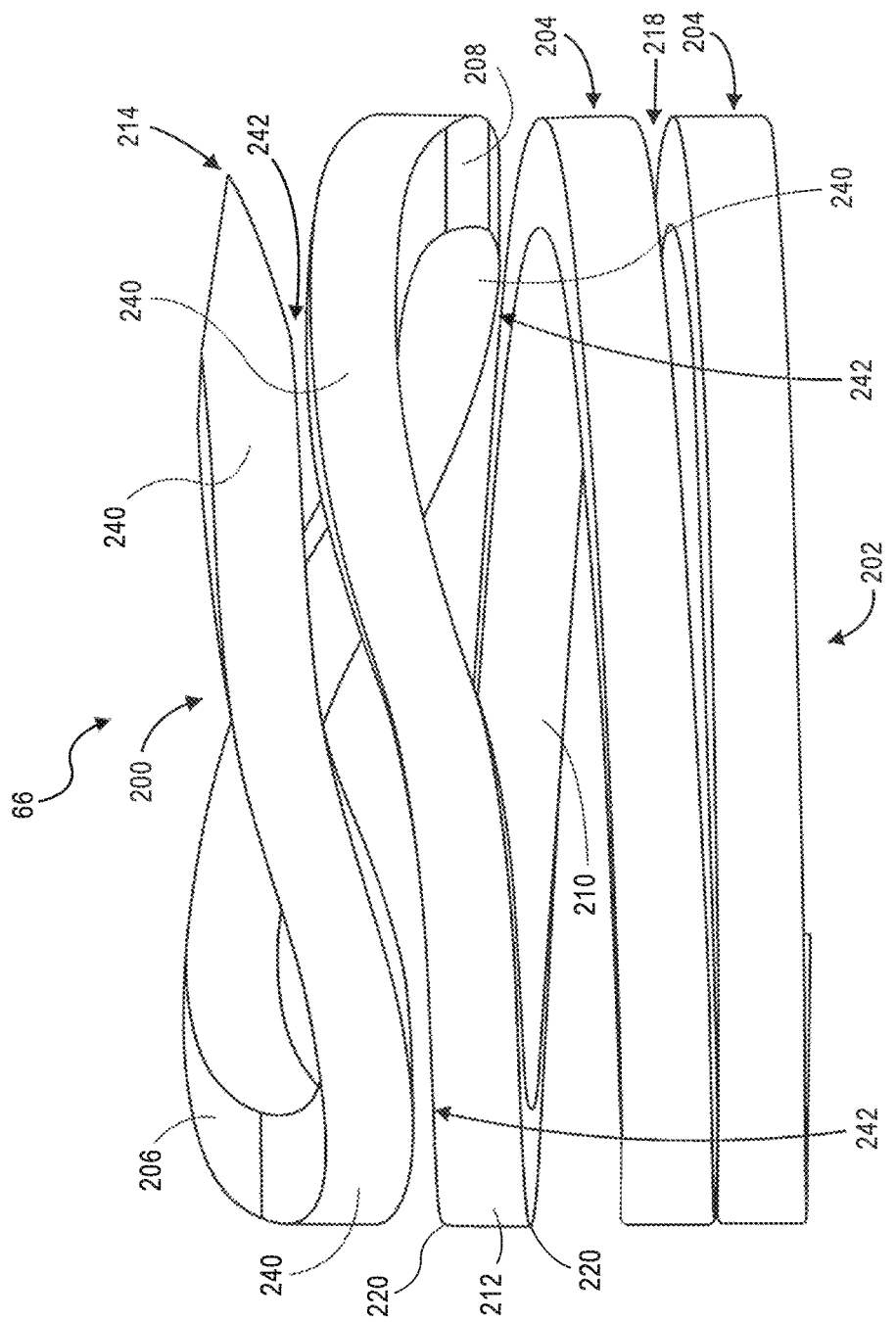
FIG. 12 is a side elevation of an embodiment of the tube-cut helical fixation anchor employing localized compression points to increase tissue fixation and reduce the risk of device dislodgement.

FIG. 12 is a side elevation of an embodiment of the tube-cut helical fixation anchor 66 employing localized compression points to increase tissue fixation and reduce the risk of device dislodgement. As shown in FIG. 12, the pitch of the helical configuration of the turns 204 of the tube-cut helical anchor 66 is not uniform along its route, resulting in distal-proximal bends or humps 240 in various turns 204 of the helical configuration. The distal-proximal bends 240 result in constricted areas 242 between adjacent turns 204 wherein the helical gap space 218 cut into the tubular body 150 (see FIG. 5) in making the helical turns 204 of the anchor 66 is more narrow distal-proximal than at other locations along the helical configuration where the bends 240 are absent. These constricted spaces 242 provided localized tissue compression points that help the helical anchor 66 to hold the tissue and not dislodge from the tissue.

Figure 13:
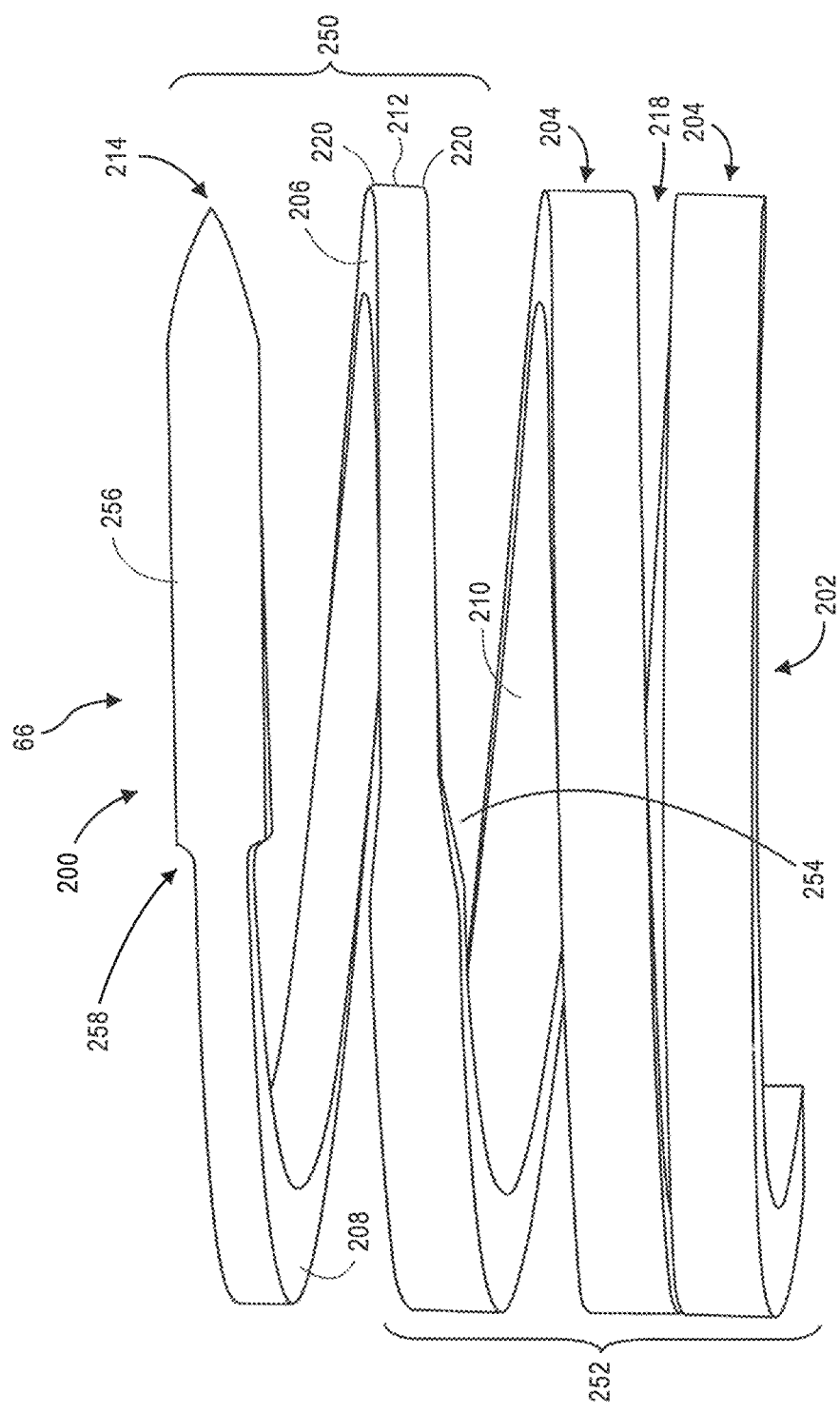
FIG. 13 is a side elevation of an embodiment of the tube-cut helical fixation anchor employing turns with varied cross-sections.

FIG. 13 is a side elevation of an embodiment of the tube-cut helical fixation anchor 66 employing turns 204 with varied cross-sections. As illustrated in FIG. 13, the tube-cut helical fixation anchor 66 incudes a distal or initial section 250 and a proximal or secondary section 252. The distal section 250 has turns 204 with a short cross-sectional height. The proximal section 252 has turns 204 with a tall cross-sectional height relative to the shorter cross-sectional height of the distal section 250. The distal section 250 transitions at a gradually tapering height transition 254 to the proximal section 252. The distal section 250 easily engages the cardiac tissue on account of the reduced cross-sectional height of its turns 204, while the larger cross-sectional height of the turns 204 of the proximal section 252 provides the proximal section 252 with increased rigidity and holding strength against the cardiac tissue.

The distal section 250 may also include a barbed tip segment 256 that has a portion of a turn 204 with a cross-section height at least generally the same as the cross-section height of the turns 204 of the proximal section 252 and extends proximally along the helical configuration of the anchor 66 from the distal tip 214 to an abrupt transition 258 to the short cross-sectional height of the turns 204 of the distal section 250, This barbed tip 256 and its abrupt transition 258 increase tissue attachment and help to mitigate device dislodgement.

Figure 14:
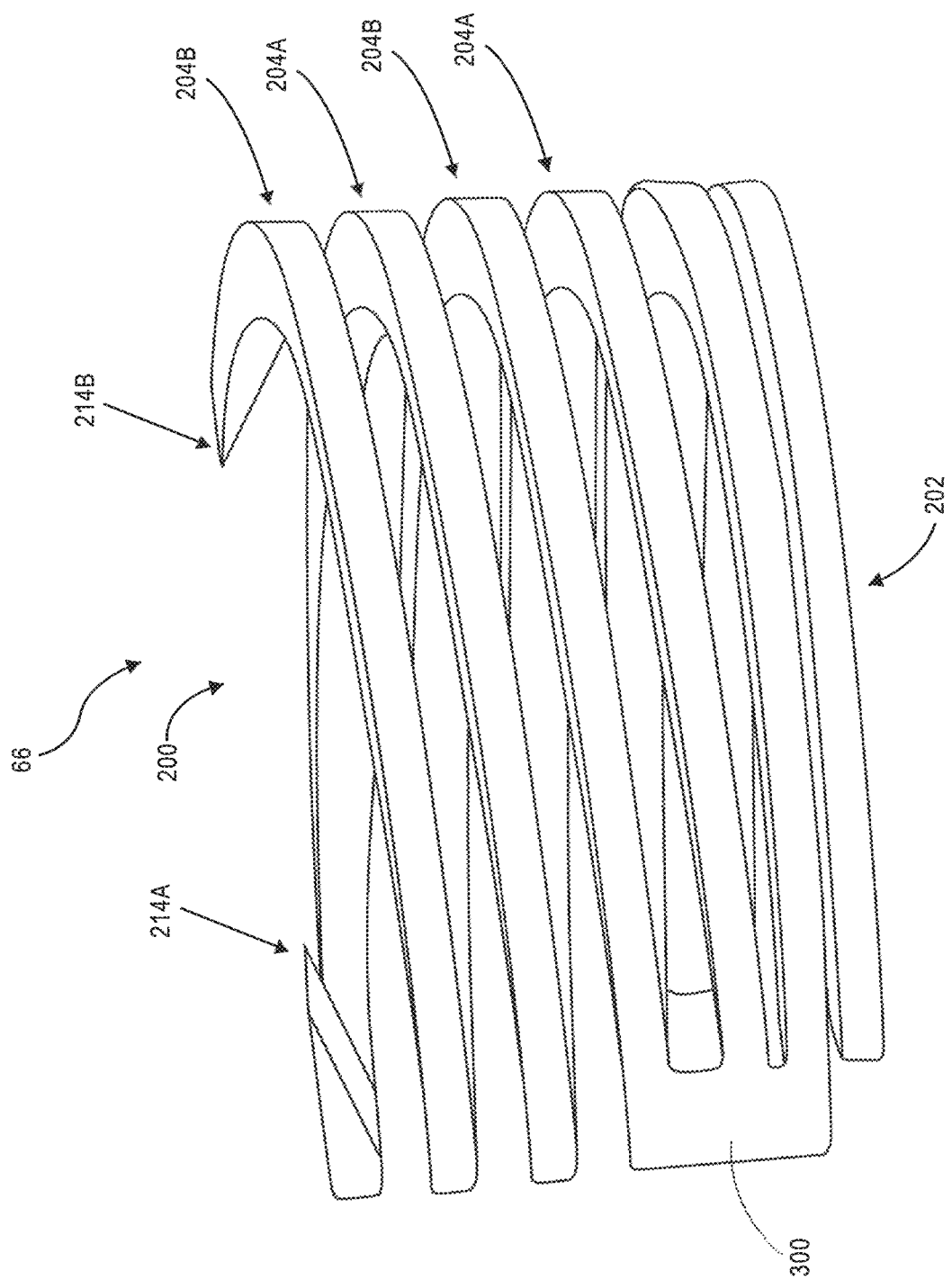
FIG. 14 is a side elevation of an embodiment of the tube-cut helical fixation anchor employing dual helical arrangements cut from a single tube.

FIG. 14 is a side elevation of an embodiment of the tube-cut helical fixation anchor 66 employing dual helical arrangements cut from a single tube. In other words, the anchor 66 has a first set of helically wound turns 204A and a second set of helically wound turns 204B, wherein the first set of helically wound turns are arranged with the second set of helically wound turns in a staggered or alternating arrangement along the length of the anchor 66. The first and second sets of helically wound turns share a common base or interconnection 300 at the distal end of the anchor 66, and each set of helically wound turns terminates in its own distinct and separate distal tip 214A and 214B. These distal tips may terminate approximately 180 degrees apart from each other, as illustrated in FIG. 14. Alternatively, the distal tips may terminate at some lesser degree of separation. In some embodiments the anchor 66 may have three, four or more helical arrangements cut from a single tube, wherein the turns of such helical arrangements are arranged in a similar staggered or alternating arrangement along the length of the anchor 66.

The prior art wound-wire helical fixation anchor 1 of FIG. 1 is severely limited by the properties of the original wire 2 and the production methods of winding a helix. In contrast, the tube-cut helical fixation anchor 66 disclosed herein provides much greater design and performance flexibility, resulting in improved and safer device fixation to cardiac tissue. The tube-cut helical anchor 66 and its manufacture provides multiple opportunities to optimize fixation performance that are not possible via the prior art wound-wire helical anchor 1. For example, on account of the anchor 66 being cut from a tubular body and unlike the prior art wound-wire anchor 1, the tube-cut helical anchor 66 can incorporate secondary features, such as, for example, barbs, barbed tips, turn bumps, varying helical pitches, and varying turn heights to resist counter rotation and associated device dislodgement. The tube-cut helical anchor 66 can be of lower profile and less impactful to tissue as compared to the prior art wound-wire helical anchor 1. Finally, the tube-cut helical anchor 66 can have integrated structural features that can be used for attaching the anchor 66 to its supporting device and/or inhibiting structural collapse of the helical configuration of the anchor 66. Also, the integrated structural features of the tube-cut helical anchor 66 can reduce adverse pinching of the tissue in which the anchor 66 is received.

The foregoing merely illustrates the principles of the invention. Various modifications and alterations to the described embodiments will be apparent to those skilled in the art in view of the teachings herein. It will thus be appreciated that those skilled in the art will be able to devise numerous systems, arrangements and methods which, although not explicitly shown or described herein, embody the principles of the invention and are thus within the spirit and scope of the present invention. From the above description and drawings, it will be understood by those of ordinary skill in the art that the particular embodiments shown and described are for purposes of illustrations only and are not intended to limit the scope of the present invention. References to details of particular embodiments are not intended to limit the scope of the invention.

What is claimed is:

1. A leadless electrotherapy system, comprising:
   a leadless pulse generator including a housing containing an electronic component configured to generate an electrical pulse, a distal electrode electrically connected to the electronic component, and a header assembly separating the distal electrode from a proximal electrode; and
   a fixation anchor having a plurality of helical turns mounted on the header assembly, wherein the plurality of helical turns include a distal helical turn extending distally from a proximal helical turn, wherein a helical slot separates the distal helical turn from the proximal helical turn, wherein a wall portion interconnects the proximal helical turn and the distal helical turn across the helical slot to join the proximal helical turn to the distal helical turn, and wherein the helical slot includes a distal slot portion distal to the wall portion and a proximal slot portion proximal to the wall portion.

2. The leadless electrotherapy system of claim 1, wherein the wall portion occludes the helical slot.

3. The leadless electrotherapy system of claim 1, wherein the plurality of helical turns have non-round cross-sections.

4. The leadless electrotherapy system of claim 3, wherein the non-round cross-sections have an aspect ratio not equal to one.

5. The leadless electrotherapy system of claim 4, wherein the aspect ratio includes a cross-sectional width greater than a cross-sectional height.

6. The leadless electrotherapy system of claim 5, wherein the cross-sectional width is at least twice the cross-sectional height.

7. The leadless electrotherapy system of claim 1, wherein the proximal helical turn and the distal helical turn extend from the wall portion in a dual helical arrangement to respective distal tips.

8. The leadless electrotherapy system of claim 7, wherein the respective distal tips are separated by a degree of separation.

9. The leadless electrotherapy system of claim 1, wherein the fixation anchor includes a distal most turn terminating in a distal tip, and wherein a leading point of the distal tip is at an outer arcuate surface of the distal tip.

10. A leadless electrotherapy system, comprising:
    a leadless pulse generator including a housing containing an electronic component configured to generate an electrical pulse, a distal electrode electrically connected to the electronic component, and a header assembly separating the distal electrode from a proximal electrode; and
    a fixation anchor having a plurality of helical turns mounted on the header assembly, wherein the plurality of helical turns include a distal helical turn extending distally from a proximal helical turn, wherein a helical slot separates the distal helical turn from the proximal helical turn, and wherein a stop occludes the helical slot between the proximal helical turn and the distal helical turn to prevent further rotation of the fixation anchor into tissue of a patient.

11. The leadless electrotherapy system of claim 10, wherein the plurality of helical turns have non-round cross-sections.

12. The leadless electrotherapy system of claim 11, wherein the non-round cross-sections have an aspect ratio not equal to one.

13. The leadless electrotherapy system of claim 10, wherein the proximal helical turn and the distal helical turn extend from the stop in a dual helical arrangement to respective distal tips.

14. The leadless electrotherapy system of claim 10, wherein the fixation anchor includes a distal most turn terminating in a distal tip, and wherein a leading point of the distal tip is at an outer arcuate surface of the distal tip.

15. A method, comprising:
    cutting a helical slot into a body to form a fixation anchor having a plurality of helical turns, wherein the plurality of helical turns include a distal helical turn separated from a proximal helical turn by the helical slot, wherein a wall portion of the body is retained to interconnect the proximal helical turn and the distal helical turn across the helical slot to join the proximal helical turn to the distal helical turn, and wherein the helical slot includes a distal slot portion distal to the wall portion and a proximal slot portion proximal to the wall portion; and mounting the plurality of helical turns on a header assembly of a leadless pulse generator, wherein the leadless pulse generator includes a housing containing an electronic component configured to generate an electrical pulse, and a distal electrode electrically connected to the electronic component, and wherein the header assembly separates the distal electrode from a proximal electrode.

16. The method of claim 15, wherein the helical slot is cut into the body by a laser, and further comprising finishing a surface of the fixation anchor.

17. The method of claim 15, wherein the plurality of helical turns have non-round cross-sections.

18. The method of claim 17, wherein the non-round cross-sections have an aspect ratio not equal to one.

19. The method of claim 15, wherein the proximal helical turn and the distal helical turn extend from the wall portion in a dual helical arrangement to respective distal tips.

20. The method of claim 15 further comprising tipping a distal tip of the fixation anchor to form a leading point, wherein the leading point is at an outer arcuate surface of the distal tip.

* * * * *